(12) United States Patent
Ngo et al.

(10) Patent No.: US 8,748,641 B2
(45) Date of Patent: Jun. 10, 2014

(54) PROCESS FOR PREPARING SATURATED BRANCHED CHAIN FATTY ACIDS

(75) Inventors: Helen Ngo, North Wales, PA (US); Thomas A. Foglia, Lafayette Hill, PA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 513 days.

(21) Appl. No.: 12/774,347

(22) Filed: May 5, 2010

(65) Prior Publication Data

US 2011/0275844 A1   Nov. 10, 2011

(51) Int. Cl.
*C07C 51/36* (2006.01)

(52) U.S. Cl.
USPC .............................. 554/142; 554/124; 554/125

(58) Field of Classification Search
USPC .................................. 554/124, 141, 142, 154
See application file for complete search history.

(56) References Cited

U.S. PATENT DOCUMENTS

| | | | | |
|---|---|---|---|---|
| 4,568,786 | A | * | 2/1986 | Hsia Chen et al. ............. 585/517 |
| 4,645,751 | A | * | 2/1987 | McCullen et al. .............. 502/37 |
| 4,658,079 | A | * | 4/1987 | Chen .............................. 585/517 |
| 5,026,933 | A | * | 6/1991 | Blain et al. ..................... 585/7 |
| 5,677,473 | A | | 10/1997 | Tomifuji et al. |
| 5,713,990 | A | | 2/1998 | Erhan et al. |
| 6,455,716 | B2 | * | 9/2002 | Kenneally et al. ............. 554/158 |
| 6,831,184 | B2 | * | 12/2004 | Zhang et al. ................... 554/158 |
| 6,946,567 | B2 | | 9/2005 | Zhang et al. |
| 7,119,216 | B2 | | 10/2006 | Newman et al. |
| 2003/0191330 | A1 | | 10/2003 | Zhang et al. |
| 2010/0022664 | A1 | | 1/2010 | Papadogianakis et al. |

OTHER PUBLICATIONS

Ngo, H.L., et al., Zeolite-catalyzed isomerizatin of oleic acid to branched-chain isomers, 2007, Eur. J. Lipid Sci. Technol., 108, pp. 214-224.*

Ngo, H.L. et al., Zeolite-catalyzed isomerizatin of oleic acid to branched-chain isomers, 2007, Eur. J. Lipid Sci. Technol., 108, pp. 214-224.

* cited by examiner

*Primary Examiner* — Yate K Cutliff
(74) *Attorney, Agent, or Firm* — John D. Fado; G. Byron Stover

(57) ABSTRACT

A process for preparing saturated branched chain fatty acids or alkyl esters thereof involving subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a stericly hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction. The yield of said saturated branched chain fatty acids is ≥70 wt %. The stericly hindered Lewis base is a tertiary amine or phosphine with linear or branched C1 to C6 alkyl or phenyl groups attached thereto.

12 Claims, 1 Drawing Sheet

PROCESS FOR PREPARING SATURATED BRANCHED CHAIN FATTY ACIDS

REFERENCE TO RELATED APPLICATION

This application claims the benefit of U.S. application Ser. No. 12/767,083, filed 26 Apr. 2010, which is incorporated herein by reference in its entirety.

BACKGROUND OF THE INVENTION

The present invention relates to a process for preparing saturated branched chain fatty acids or alkyl esters thereof involving subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a stericly hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction. The yield of said saturated branched chain fatty acids is ≥70 wt %. The stericly hindered Lewis base is a tertiary amine or phosphine with linear or branched C1 to C6 alkyl or phenyl groups attached thereto.

Environmental concerns over the use of petroleum-based materials in the lubricant industry have stimulated much research to find suitable alternatives. In this regard, lubricating fluids derived from renewable fats and oils are of interest because of their purported advantages over petroleum-based materials (Hill, K., Pure Appl. Chem., 79: 1999-2011 (2007)). Among the cited advantages of fatty acid derived lubricants are their lower toxicity, lower flammability since they have lower vapor pressures, and better biodegradability compared to petroleum-based materials. Potential applications for such bio-based fluids can range from lubricants, greases, additives, polymers, organic chemicals and more. In fact, there are many commercial products in the market that are derived from renewable resources. For instance, polylactide polymers and 1,3-propanediol, important intermediates for polymer syntheses, are derived from biomass sugars by fermentation and are cost competitive with petroleum-based materials (Carole, T. M., et al., Applied Biochem. and Biotech., 113-116: 871-885 (2004)).

Vegetable oils also are promising candidates as replacements for petroleum-based materials since they have excellent lubricity properties (Swern, D., Baily's Industrial Oil and Fat Products, Third Edition, John Wiley & Sons, New York). Although these oils themselves have some commercial use, it is limited due to the presence of double bonds within their fatty acid alkyl chains which lead to oxidative stability problems when used at high temperature. Over the past decades, numerous chemical methods including electrophilic, nucleophilic, oxidative, and metal-catalyzed reactions have been developed that convert the common fatty acids found in natural fats and oils to novel oleochemical compounds that have improved and/or new properties over the starting fatty acids. For example, chemical processes for the modification of soy oil for use in greases, hydraulic and drilling fluids, and printing inks have been developed (Erhan, S. Z. and M. O. Bagby, J. Am. Oil Chem. Soc., 68(9): 635-638 (1991); Erhan, S. Z., et al., J. Am. Oil Chem. Soc., 69(3): 251-256 (1992); U.S. Pat. No. 5,713,990).

Saturated branched-chain fatty acid isomers (sbc-FAs), commonly referred to as isostearic acids, are derived from unsaturated fats and oils as a mixture of mono-methyl branched fatty acids (2, FIG. 1). Such mixtures of fatty acids are of commercial interest because they are liquid at low-temperatures, have good lubricity properties, and have good oxidative stabilities because of their lack of double bonds. Isostearic acid type products are currently used in the formulation of cosmetics, body washes, lubricants and fuel additives, surfactants, soaps, and coatings. Approximately 100 million pounds of these acids are consumed globally each year. Currently, the bulk of sbc-FAs 2 are obtained as coproducts from reactions that predominantly produce dimer fatty acids (6, FIG. 1). The typical yields of sbc-FAs 2 are 25-50 wt %, and their isolation and purification from the dimer acid 6 are labor-intensive. New processes that give higher yields and higher selectivity of sbc-FAs at a lower cost and with improved ease of isolation from other coproducts would be highly advantageous; such processes would expand their present use and/or open new outlets for these type of fatty acids.

We have developed a more efficient and economical process that maximizes sbc-FAs production and minimizes the bimolecular reactions that produce dimer products 6 as well as other unwanted coproducts (stearic 3, hydroxystearic 4, and γ-stearolactone 5; FIG. 1). We have also improved catalyst stability for multiple reuses.

SUMMARY OF THE INVENTION

In accordance with the present invention there is provided a process for preparing saturated branched chain fatty acids or alkyl esters thereof involving subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a stericly hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction. The yield of said saturated branched chain fatty acids is ≥70 wt %. The stericly hindered Lewis base is a tertiary amine or phosphine with linear or branched C1 to C6 alkyl or phenyl groups attached thereto.

DETAILED DESCRIPTION OF THE INVENTION

Figure 1:
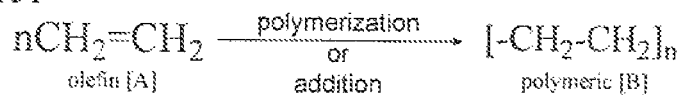
FIG. 1 shows products produced from zeolite-catalyzed isomerization of oleic acid as described herein.
Figure 2:
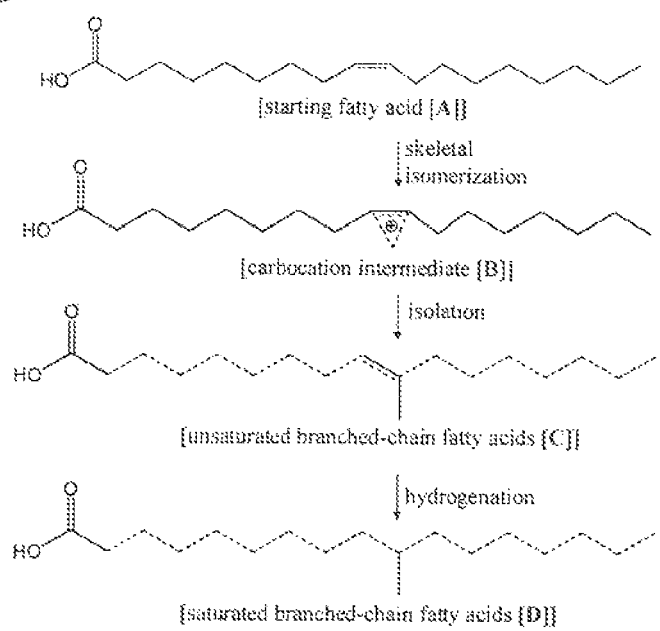
FIG. 2 shows GC spectra of the isomerized, hydrogenated and methylated product mixtures as described below: (A) with 2.5 wt % H-Ferr zeolite; (B) with 8 wt % H-Mordenite zeolite. Tridecanoate was the internal standard. 2=methyl isostearate; 3=methyl stearate; 4=methyl hydroxystearate; 5=γ-stearolactone; 6=C36-methyl ester dimer.

The present invention concerns a process for preparing saturated branched-chain fatty acids or alkyl esters thereof. The process involves the steps of subjecting an unsaturated fatty acid or ester having 10 to 25 carbon atoms, or mixtures of unsaturated fatty acids or esters to a skeletal isomerization reaction in the presence of water or a lower alcohol at a temperature of about 240° to about 280° C. (e.g., 240°-280° C.) using a combination of a sterically hindered Lewis base and a zeolite as a Brönsted or Lewis acid catalyst; the reaction time is generally about 4 to about 8 hours (e.g., 4-8 hours) and the amount of Lewis base utilized is generally about 2.5 wt % to about 20 wt % (e.g., 2.5 wt % to 20 wt %) to zeolite). The isomerized fatty acid mixture is then subjected to hydrogenation to remove remaining double bonds within the fatty acid or ester chains to produce saturated branched-chain fatty acid or ester mixtures. The zeolite catalysts used in the process has a linear pore structure with a pore size that is small enough to retard oligimerization of unsaturated fatty acids or esters but sufficiently large enough to allow diffusion of the fatty acids or alkyl esters thereof into the zeolite structure where fatty acid or ester chain isomerization is catalyzed, The branched chain fatty acids or alkyl esters or mixtures thereof are then isolated from the reaction mixture and the isomerized fatty acid or ester or mixtures thereof hydrogenated to remove residual unsaturation yield the desired saturated branched-chain fatty acid or ester mixture. The yield of the saturated branched-chain fatty acids is typically ≥70 wt %. The sterically hindered Lewis base is, for example, a tertiary amine or phosphine with linear or branched C1 to C6 alkyl or phenyl groups attached thereto.

When a starting material mixture contains both unsaturated fatty acids or alkyl esters thereof, both branched chain fatty acids and alkyl esters thereof can be produced because both can be isomerized simultaneously. The isomerization of unsaturated fatty acid case is included in the present invention.

The unsaturated fatty acid used as the starting material is generally a fatty acid having unsaturated bonds and a total carbon number of 10 to 25, preferably a total carbon number of 16 to 22. Considering industrial applications, it is preferable that the major component of the starting material has an average carbon number of 18. Unsaturated fatty acids having a total carbon number of this range are useful as starting materials for the synthesis of sbc-FAs for use in cosmetic bases, fiber treating agents, lubricating oil additives, etc.

With respect to the degree of unsaturation (i.e., the number of unsaturated carbon-carbon bonds), any unsaturated fatty acid may be used as long as one or more such bonds are present in the molecule. Specifically, the number of unsaturated bonds is generally 1 to 3, preferably 1. Octadecenoic acid is the most preferable. The presence of an unsaturated bond in the molecule causes the formation of a carbocation as an intermediate, thereby facilitating the skeletal isomerization reaction. If a saturated fatty acid is used in large quantities as a starting material, formation of this intermediate carbocation is hampered, thereby making it difficult for isomerization to proceed.

Unsaturated fatty acids include oleic acid, palmitoleic acid, erucic acid, elaidic acid, linoleic acid, linolenic acid, and undecenoic acid, which can be derived from beef tallow, palm oil, safflower oil, sunflower oil, tall oil, rapeseed oil, soybean oil, or the like. The mixture that may be used as the starting material is a mixture containing two or more of these unsaturated fatty acids, or a mixture containing one or more of these unsaturated fatty acids and one or more saturated fatty acids such as palmitic and stearic acids, various esters of the aforementioned unsaturated fatty acids, and the like. In the case of a mixture, the content of the above-mentioned unsaturated fatty acids is generally not less than about 40% by weight (e.g., not less than 40% by weight), preferably not less than 80% by weight (e.g., not less than 80% by weight) in view of reaction rate and yield.

From the viewpoint of reaction selectivity, it is preferable that the above-described starting material contains about 40 to about 100% by weight (e.g., 40 to 100% by weight) of octadecenoic acids, such as oleic acid and elaidic acid.

Alkyl esters of unsaturated fatty acids having a total carbon number of 10 to 25 used as a starting material are those corresponding to the above-described unsaturated fatty acids. That is, alkyl esters of the unsaturated fatty acids exemplified above are used. Although the alkyl moiety is not subject to limitation as to carbon number, its carbon number is normally 1 to 3, preferably 1. Specific examples of alkyl esters include methyl esters, ethyl esters, propyl esters, and butyl esters of the above-mentioned unsaturated fatty acids, with preference given to methyl esters.

When a mixture is used as the starting material, a mixture that contains at least one alkyl ester of the above-described fatty acids is used. Specifically, it is a mixture of one or more alkyl esters of these unsaturated fatty acids, or a mixture containing at least one alkyl ester of these unsaturated fatty acids and saturated fatty acids, various esters, etc. In the case of a mixture, the content of alkyl esters of the above-mentioned unsaturated fatty acids is normally not less than about 40% by weight (e.g., not less than 40% by weight), preferably not less than 80% by weight (e.g., not less than 80% by weight) in view of reaction rate and yield.

From the viewpoint of reaction selectivity, it is preferable that the above-described starting material be alkyl esters of unsaturated fatty acids containing about 40 to about 100% (e.g., 40 to 100% by weight) by weight of alkyl esters of octadecenoic acid, such as methyl oleate and methyl elaidate, or a mixture thereof.

The present invention utilizes a combination of (1) zeolite as a Brönsted or Lewis acid catalyst and (2) a stericly hindered Lewis base. The Lewis base has a molecular size larger than the largest dimension of the open channels of the zeolite; the Lewis base interacts with the external active sites on the surface of the zeolite framework but because of their molecular size have limited access to the active sites within the zeolite channels. Such bases can neutralize the external acidic sites on the surfaces of the zeolite framework but because of their size cannot access the interior acidic sites in the channels. The Lewis base may be an amine, phosphine, triarylphosphine, dialkylarylphosphine, trialkylphosphine, or mixtures thereof. The phosphine may be methylphosphine, butylphosphine, dibutylphosphine, tributylphosphine, phenylphosphine, diphenylphosphine, or mixtures thereof. The triarylphosphine may be triphenylphosphine, diphenylphosphine, tri-p-tolylphosphine, tri(o-tolyl)phosphine, tri-m-tolylphosphine, trixylyl-phosphine, tris(p-ethylphenyl)phosphine, tris(p-methoxyphenyl)phosphine, tris(4-fluorophenyl)phosphine, tris(4-methoxyphenyl)phosphine, tris(dimethylamino)phosphine, tris(trimethylsilyl)phosphine, triisopropylphosphine, or mixtures thereof. The dialkylarylphosphine may be di-n-butylphenylphosphine, dicyclohexylphenylphosphine, or mixtures thereof. The trialkylphosphine may be tri-n-butylphosphine, tricyclohexylphosphine, tri-n-octylphosphine, trimethyphosphine, triethylphosphine, triisopropylphosphine, tricyclopentylphosphine, or mixtures thereof. The amine may be dimethylamine, trimethylamine, diethylamine, triethylamine, diisopropylamine, triisopropylamine, triphenylamine, diphenylamine, or mixtures thereof.

Zeolite used for the present invention has a linear pore structure of pore size which is small enough to retard dimerization and large enough to allow diffusion of branched chain fatty acids or alkyl esters thereof. Significant by-product formation due to dimerization is undesirable because it results in decreased yield of branched chain fatty acids, etc. However, insufficient diffusion of branched chain fatty acids, etc. is also undesirable because it results in decreased apparent catalyst activity. To meet the above requirements, the mean pore size of zeolite is normally about 4 to about 9 Angstroms (e.g., 4 to 9), preferably about 5 to about 8 Angstroms (e.g., 5 to 8), and more preferably about 6 to about 7 Angstroms (e.g., 6 to 7), varying depending on the total carbon number of branched chain fatty acids, etc. The term "linear pore structure" as used herein is a structure wherein pores are formed by at least linear continuous pathways.

In the present invention, any zeolite can be used, as long as it meets the above requirements. Generally, ferrierite type zeolite and mordenite type zeolite are preferred from the viewpoint of pore size, heat resistance, acid resistance, and acid properties. The former is available only as a synthetic substance; the latter is available both as a natural substance and as a synthetic substance. The term "ferrierite type zeolite as used herein, is a zeolite composed of two-dimensional aluminum-silica network structure, with interconnecting channels between the 8-membered-ring (MR) and 10-MR structures (Bekkem, H. V., Introduction to Zeolite Science and Practice, 2nd Edition, Elsevier, New York, N.Y., 2001, pp. 1033-1053). The channels of commercially available Ferrierites typically contain an alkali metal (Na or K) or ammonium ($NH_4$) cation. For example, we examined K-containing Ferrierite with a silica/alumina (Si/Al) molar ratio of 17.5. The mordenite type zeolite, the highest in silicon content among naturally-occurring zeolites, is a zeolite composed of oxygen 12-membered ring wherein the pores are formed mainly by tunnel-like pore pathways (Shokubai Koza, Vol. 10, edited by the Catalysis Society of Japan, Kodansha Ltd. (1986)). Although these zeolites can be synthesized by hydrothermal synthesis (J.C.S., 2158 (1948)), they are also commercially available.

Although it is preferable from the viewpoint of catalyst activity that the cation in zeolite be a proton, a zeolite of the sodium type, or the like, may be used in the reaction after being converted into the proton type by ion exchange. The Si/Al molar ratio of zeolite is preferably about 3 to about 300 (e.g., 3 to 300), more preferably about 5 to about 100 (e.g., 2 to 100). The ratio is preferably not less than about 3 (e.g., not less than 3) in view of catalytic activity, and not more than about 300 (e.g., not less than 300) in view of yield. The "silica/alumina ratio (molar)" can easily be determined by atomic absorption photometry. Zeolite may be used in the reaction after a pretreatment by ion-exchange, drying or burning.

In the present invention employing the above-described zeolite, the reaction is carried out in the presence of water or a lower alcohol. This is to suppress acid anhydride formation due to dehydration or dealcoholation of the starting material. This suppression is attributable to acid point modification of zeolite, such as conversion of Lewis acid point into Brönsted acid point. It is preferable to add water when the starting material is unsaturated fatty acids; and an alcohol when the starting material is esters of unsaturated fatty acids. The lower alcohol used is exemplified by alcohols having 1 to 4 carbon atoms. Specifically, methanol, ethanol, propanol, butanol etc. are preferred, with a greater preference given to those having the same alkyl group as that of the starting fatty acid esters to be isomerized.

The isomerization reaction step in the present invention is carried out using the above-described starting material, zeolite, etc. As for specific reaction conditions, it is preferable that the reaction be carried out at about 240° to about 280° C. (e.g., 240° to 280° C.) in the presence of about 0.1 to about 30 parts by weight (e.g., 0.1 to 30 parts by weight) of zeolite and about 0.5 to about 5 parts by weight (e.g., 0.5 to 5 parts by weight) of water or a lower alcohol, based on about 100 parts by weight (e.g., 100 parts by weight) of the above-described unsaturated fatty acids and/or alkyl esters thereof. More preferably, the reaction is carried out at about 240° to about 280° C. (e.g., 240° to 280° C.) in the presence of about 1 to about 20 parts by weight (e.g., 1 to 20 parts by weight) of zeolite and about 1 to about 3 parts by weight (e.g, 1 to 3 parts by weight) of water or a lower alcohol, based on about 100 parts by weight (e.g., 100 parts by weight) of the above-described unsaturated fatty acids and/or alkyl esters thereof.

Also, the reaction may be carried out in a closed system where the reaction pressure is generally about 2 to about 50 $kgf/cm^2$ (e.g., 2 to 50 $kgf/cm^2$). This is to prevent vaporization of water, alcohols and other low boiling substances in the system including those substances contained in a catalyst.

Since the catalyst tends to be poisoned by coke, the reaction normally takes about 1 to about 10 hours (e.g., 1 to 10 hours). If this problem is overcome, the reaction time can be shortened to several minutes or even several seconds. Also, continuous reaction becomes possible. Excessively long reaction time tends to cause thermal decomposition, resulting in decreased yield.

The reaction apparatus used is preferably an autoclave, because a pressurized reaction system is preferred. The atmosphere in the autoclave is preferably replaced with nitrogen or argon.

The product obtained by the above-described isomerization reaction contains branched chain unsaturated fatty acids and/or esters thereof, when the starting material is an ester of an unsaturated fatty acids, in a high yield. The product further contains polymeric fatty acids, such as dimer acids (polymeric fatty acid esters, when the starting material is esters of unsaturated fatty acids). The branched chain fatty acids, etc. thus obtained normally have alkyl side chains of 1 to 4 carbon atoms. They are obtained as a mixture of many isomers with different branching positions.

Furthermore, in the present invention, branched chain saturated fatty acids (esters of branched chain saturated fatty acids, when the starting material is esters of unsaturated fatty acids) can be obtained as follows. Namely, removal of catalyst zeolite and polymeric materials by filtration or distillation, the residue is hydrogenated in an autoclave by a known method, such as the method using a hydrogenation catalyst (e.g., nickel or palladium/carbon), to yield a mixture of crude branched chain saturated fatty acids (esters of branched chain fatty acids, when the starting material is esters of unsaturated fatty acids). Then the crude product is purified by removing linear chain components by a known method, such as the compression method, the Emerson method, and the Henkel method (U.S. Pat. No. 2,293,674; U.S. Pat. No. 2,421,157; U.S. Pat. No. 2,800,493; J. Am. Oil Chem. Soc., 45, 471 (1968)) or recrystallization method, to yield branched chain saturated fatty acids (esters of branched chain saturated fatty acids, when the starting material is esters of unsaturated fatty acids) of high purity.

The yield of the saturated branched chain fatty acids is generally >about 70 wt % (e.g., >70 wt %); preferably >about 71 wt % (e.g., >71 wt %); preferably >about 72 wt % (e.g., >72 wt %); preferably >about 73 wt % (e.g., >73 wt %); preferably >about 74 wt % (e.g., >74 wt %); preferably >about 75 wt % (e.g., >75 wt %); preferably >about 76 wt % (e.g., >76 wt %); preferably >about 77 wt % (e.g., >77 wt %); preferably >about 78 wt % (e.g., >78 wt %); preferably >about 79 wt % (e.g., >79 wt %). The yield of dimers (e.g., 6 in FIG. 1) is generally <about 15 wt % (e.g., <15 wt %); preferably <about 14 wt % (e.g., <14 wt %), <about 13 wt % (e.g., <13 wt %), <about 12 wt % (e.g., <12 wt %), <about 11 wt % (e.g., <11 wt %), <about 10 wt % (e.g., <10 wt %), <about 9 wt % (e.g., <9 wt %), <about 8 wt % (e.g., <8 wt %), <about 7 wt % (e.g., <7 wt %), <about 6 wt % (e.g., <6 wt %), <about 5 wt % (e.g., <59 wt %).

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

The oleic acids 1 used in this study were a commercially available material (Priolene™ 6936: 92.3 wt % oleic (C18:1), 3.1 wt % linoleic (C18:2), 0.4 wt % linolenic (C18:3), 4.2 wt % saturated fatty acids); a gift from Croda International Co. (Gouda, The Netherlands)) and a laboratory grade oleic acid (91.2 wt. % C18:1, 6.1 wt. % C18:2, 2.7 wt. % saturated fatty acids), from Aldrich Chemical (Milwaukee, Wis.). Triphenylphosphine (TPP), hydrochloric acid (HCl), sulfuric acid ($H_2SO_4$), acetone, hexane, and methanol (MeOH) were from Aldrich Chemical. Mordenite (HSZ-640HOA, protonated ($H^+$), 17.5-19.5 mol/mol $SiO_4/AlO_4$) and Zeolite Ferrierite (HSZ-720KOA, potassium ($K^+$), 17.5 mol/mol $SiO_4/AlO_4$) were purchased from Tosoh Co. (Tokyo, Japan). All other reagents used were of the highest purity available from commercial suppliers.

Zeolite Catalyst Treatment: Solid $K^+$-Ferrierite zeolite was ion-exchanged using the procedure described by Ngo et al. (Ngo, H. L., et al., Eur. J. Lipid Sci. Technol., 108: 214-224 (2007)) but with some parts of the procedure modified. $K^+$-Ferrierite zeolite (100 g) was triturated with 300 mL of 1N HCl and 100 mL of deionized water at 55° C. for ~20 h. The proton exchanged $K^+$-zeolite was centrifuged (3000×g), washed by resuspention in deionized water (500 mL×5). The supernatant tested with pH paper. The pH of the supernatant solution was neutral after the fifth wash. The solid was dried in an oven at 115° C. for 20 h. Approximately 90 g of white solid was obtained. The ion-exchange treatment converted the $K^+$-zeolite into a Ht zeolite (the $K^+$-zeolite solid does not catalyze the isomerization reaction).

Synthesis and characterization of sbc-FA products: Sbc-FA products 2 were obtained using conditions as previously reported (Ngo, H. L., et al., Eur. J. Lipid Sci. Technol., 108: 214-224 (2007)) but with some parts of the procedure modified. In general, a mixture of oleic acid 1 (Priolene™, 50 g), $H^+$-Ferr (2.5 g, 5 wt % of oleic acid), deionized water (1.8 mL), and TPP (7.5 wt % to $H^+$-Ferr, 188 mg) was placed into a 600 mL high pressure stainless-steel vessel (Parr Instrument, Moline, Ill.) equipped with a mechanical stirrer and an electric heating mantle with temperature controller for isomerization reaction. The vessel was sealed and purged with 7.03 kgf/cm² $N_2$ (3× for 15 min). The reactor was filled with $N_2$ to ~7.03 kgf/cm² and then heated to the desired temperature (240° C. to 280° C.) while mixing the contents. The pressure at the desired temperature was 14 to 28 kgf/cm². At the end of the reaction time (4-8 h), the reactor was cooled to room temperature, the pressure was released, and $H^+$-Ferr solids were removed by vacuum filtration using hexane and 0.45 μm HA membrane Filter™ (Millipore Co, Billerica, Mass.).

To characterize the isomerized crude unsaturated branched-chain (ubc)-FA products, 1 g of reaction liquid was hydrogenated using 5 wt % palladium on carbon (Pressure Chemical Co., Pittsburgh, Pa.) as catalyst to give a mixture of sbc-FA products. The product mixture was then methylated to give a mixture of sbc-fatty acid methyl esters (sbc-FAME) that were characterized by the following spectroscopies: Hewlett Packard (HP) Model 6890 gas chromatography instrument (GC, currently Agilent Technologies, Santa Clara, Calif.), HP 5890 GC-mass spectrometry (GC-MS), matrix-assisted laser desorption/ionization-time of flight (MALDI-ToF) with a 4700 Proeomics Analyzer (Applied Biosystems, Framingham, Mass.), varian Gemini 200 MHz nuclear magnetic resonance (NMR) (Palo Alto, Calif.), and inductively coupled plasma atomic emission spectroscopy (ICP-AES). GC was used to determine the weight percent compositions of the crude sbc-FA products (FIG. 1). GC-MS was used to determine the molecular ions of the monomeric C18-components (2, 3, 4 and 5). Mass spectra of the C36-methyl ester dimer 6 were acquired by MALDI-ToF. NMR and ICP-AES were used to determine whether any phosphorous compounds were leached into either the aqueous phase or oil products, respectively.

Zeolite Catalyst Regeneration: The used $H^+$-Ferr catalyst (2.5 g) recovered from the isomerization process was transferred into a 150 mL centrifuge flask with 1N HCl (5 mL) and deionized water (100 mL). The suspension was stirred at 55° C. for 24 h, cooled to room temperature and centrifuged (3000×g). The aqueous phase was decanted into a vacuum filtration device with a 0.45 μm HA membrane filter to capture the residual fine solid particles in the aqueous phase that did not settle to the bottom of the flask during centrifugation. The solids in the centrifuge flask were resuspended in deionized water (100 mL), mixed well, and centrifuged. This step was repeated once more and the supernatant tested with pH paper. The pH of the supernatant solution was neutral after the second wash. The light brown $H^+$-zeolites were dried at 115° C. for 20 h before reuse.

Zeolite Catalyst Reuse Experiments: The recovered regenerated $H^+$-Ferr solid catalyst (2.5 g) was mixed with oleic acid (Priolene™, 50 g), deionized water (1.8 mL), and TPP (5 wt % to $H^+$-Ferr (125 mg)) in a 600 mL Parr reactor. The mixture was purged with $N_2$, sealed under $N_2$, stirred, and heated to 260° C. for 4 h. Isolation and characterization of the product mixture were performed using the above procedures.

Analysis of Sbc-FAME: GC was used to determine the wt % composition of products in the crude isomerized reaction mixtures after hydrogenation and methylation. GC was equipped with a capillary inlet injector (on column mode) and flame ionization detector. The capillary column used was a HP Agilent DB5-HT column (30 m×0.1 mm×0.32 μm) attached to an Alltech Co., (State College, Pa.) deactivated fused silica guard column (2 m×0.32 μm). Helium was the carrier gas set at constant flow of 6 mL/min. The detector temperature was set at 390° C. The oven temperature profile used was as follow: initial temperature 50° C., hold for 1 min.; ramp at 15° C./min. to 160° C.; ramp at 7° C./min. to 230° C.; ramp at 30° C./min. to 380° C. hold for 10 min. The analytical method reported previously (Ngo, H. L., et al., Eur. J. Lipid Sci. Technol., 108: 214-224 (2007)) for characterizing crude sbc-FAME mixtures (FIG. 1) obtained from the zeolite-catalyzed isomerization of oleic acid was not sensitive enough to quantitate the dimer acid methyl ester coproduct 6 in the crude product mixture. This is because 6 has higher molecular weight ($[M]^+$=596 determined by MALDI-ToF) than the monomic C18-components (2, $[M]^+$=298, 3, $[M]^+$=298, 4, $[M]^+$=314, and 5, $[M]^+$=282 determined by GC/MS). In this regard, the chromatographic peaks for 6 were much broader than the peaks for the monomer products, which made quantitation of the former peaks difficult. To improve the resolution and hence the quantitation of the chromatographic peaks of 6 the analytical method was modified. The GC column helium flow was set at a constant flow of 6 mL/min. This minor change enhanced the chromatographic resolution of the dimer ester coproducts and allowed for their quantitation.

Results and discussion: Table 1 (entries 1 & 2) list the results obtained for the analysis of the crude ester product reported previously (Ngo, H. L., et al., Eur. J. Lipid Sci. Technol., 108: 214-224 (2007)) and when using the modified analytical method. With the new analytical method, there was about 14 wt % dimer ester 6 in the crude product mixtures compared to the 5.5 wt % reported previously. The optimized analytical method detected the dimer coproducts at concentrations ≥2 wt % in the crude mixture which is important in that our improved isomerization process only generates minor amounts of dimer ester coproducts (7.24% or less in Table 1).

One of our goals was to modify the zeolite catalyst in such a way so as to retain its activity while also enhancing its selectivity. Without being bound by theory, we hypothesized that formation of the dimer acids 6 from oleic acid 1 arises via a bimolecular reaction that is catalyzed primarily by the Brönsted acid sites located on the external surfaces of the H-Ferr particles, whereas formation of the monomer products sbc-FAs 2, hydroxystearic acid 4, and γ-stearolactone 5 was postulated to be catalyzed by all Brönsted acid sites. The stearic acid 3 was also found in the product mixture because of two reasons: 1) 2.7-4.2 wt % of 3 was already present in the starting fatty acids and 2) if the reactions gave low conversions of oleic acid, thus hydrogenation of the oleic acid would further enhance the amount of stearic acid 3. Without being bound by theory, we theorized that inactivating the active acidic sites on the external surfaces of H-Ferr particles with a Lewis base might suppress dimer acid 6 formation from oleic acid 1. With a judicious choice of Lewis base, for example one that was sufficiently bulky enough to be unable to penetrate deeply into the internal zeolite structure, we hypothesized that the acidic sites within the channels of the zeolite would remain active. If this could be accomplished, then such modification would not significantly affect the activity of skeletal isomerization of oleic acid 1 that occurs within the interiors of the zeolite framework.

Initial results surprisingly showed that the addition of small amounts of a Lewis base such as TPP to the isomerization reaction significantly reduced the formation of unwanted dimer acids. For example, in the presence of 2.5 wt % of TPP (relative to zeolite catalyst) at 250° C., the amount of dimer product 6 was surprisingly reduced from 13.6 wt % to 6.33 wt % (Table 1, entries 2 & 4). However, a longer reaction time of 22 hours (entry 4) versus 6 hours (entry 3) was needed to obtain a similar degree of conversion of oleic acid 1 to products (Table 1, entries 2 and 4). We then increased the amount of TPP from 5 to 20 wt % (entries 5 & 6 respectively) to see whether the dimer acids could be reduced to less than 5 wt %. However, little difference in product distribution was observed although a slight decrease in conversion was noted (Table 1, entry 6). It was subsequently found that increasing the reaction temperature from 250° C. to 280° C. surprisingly improved the conversion of oleic acid 1 to products (Table 1, entries 7-13). At 280° C., the TPP additive had a surprisingly significant affect on the isomerization reaction. As listed in Table 1 (entry 7), when the reaction was performed with 2.5 wt % H-Ferr without TPP, the wt % selectivity of the oleic acid to the products was 2, 66.5 wt %; 3, 4.46 wt %; 4, 5.49 wt %; 5, 0.75 wt %; and 6, 22.8 wt %. With 2.5 wt % TPP (Table 1, entry 8) added to the isomerization process the conversion to dimer acids surprisingly deceased to 7.24 wt % while the conversion to sbc-FAs 2 increased to 76.9 wt % with products 3, 4, and 5 amounting to 5.98, 7.87, and 2.01 wt % respectively. Additions of 5 to 20 wt % TPP (Table 1, entries 9-13) also were examined to see if the dimer coproduct 6 could be further reduced but minor difference in product distribution was observed from those reactions run with 2.5 wt % TPP (Table 1, entry 8). Table 1 (entries 10 & 11) show a set of two replicates, this was done to show the reproducibility of the reaction. Table 1 (entry 13) lists the reaction product distribution when performed on a 200 gram scale. The results were similar to those obtained at the 50 gram scale level (Table 1, entry 12).

We also found that this strategy worked with other types of zeolite catalysts, highlighting the potential of external "deactivation" or "neutralization" of zeolite acidic surface (external) sites. For example in a previous study by Tomifuji et al. (U.S. Pat. No. 5,677,473), it was reported that an H-Mordenite zeolite could be used to isomerize oleic acid to sbc-FAs. We performed this reaction under conditions reported by Tomifuji et al; however, the results obtained were significantly different from that reported by Tomifuji et al. Without being bound by theory, this could be due to the difference in catalyst, equipment and/or methods of product analysis. Thus, it is better to compare the experiments run with and without TPP (entries 1 to 4) since both experiments were performed using the same fatty acids, catalysts and equipment. Without TPP additive, at 280° C. for 6 h, 25.6 wt % yield of dimer coproduct 6 was obtained (Table 2, entry 1) whereas with 5 wt % of TPP added to the reaction the conversion to dimer coproduct 6 was surprisingly 14.1 wt % (Table 2, entry 2). Increasing the TTP to 10 wt % surprisingly resulted in about 9.81 wt % of dimer 6 (Table 2, entry 3). The reaction also was performed at 250° C. for 6 h to examine whether the conversion of oleic acid 1 to dimer product 6 was influenced by the reaction temperature. The results obtained were not as good as the reaction performed at 280° C.; product yields were 2, 68.3 wt %; 3, 14.5 wt %; 4, 3.6 wt %; 5, 5.82 wt % and 6, 7.78 wt %, with an oleic acid conversion of 91% (Table 2, entry 4). These results showed that sterically hindered Lewis bases like TPP played an important role in deactivating or neutralizing the external Lewis/Brönsted acid sites of the zeolites.

The use of solid catalysts in these reactions facilitated the isolation and purification of the products which should improve the economics of producing sbc-FAs. It also is important to recycle the zeolite catalysts to help reduce the overall production costs. Several attempts were made to regenerate the catalysts. The most efficient approach involved washing the used catalysts with solvents (e.g., polar solvent like acetone or non-polar solvent like hexane) to remove adhered reaction products. The used zeolite catalyst was then transferred into a centrifuge flask containing dilute hydrochloric acid, heated at 55° C. for 24 h, recovered by centrifugation, washed with deionized water, dried in an oven to remove residual water at 115° C. for ~20 h, and reused to produce sbc-FA products. For the reuse experiments, the reactions were performed with 5 wt % H-Ferr at 260° C. for 4 h. This higher catalyst loading was needed because the reuse reactions were run at shorter reaction times. For the first use, 7.5 wt % TPP to H-Ferr catalyst was added to the reaction mixture to ensure that sufficient TPP was available to coat the external acid sites (Table 3, entry 1). For the second to the tenth reuse, 5.0 wt % TPP to H-Ferr was used because of concerns that repeated TPP loading could lead to catalyst deactivation problems (Table 3, entries 2-10). With this procedure, the used H-Ferr zeolite catalyst could surprisingly be recycled up to 10 times without significant (i.e., between about 2 to about 5 wt % (e.g., 2-5 wt %) difference per cycle) loss of activity and selectivity (Table 3). There was a slight decrease in activity after the 9th reuse due to minor catalyst loss during retreatment (Table 3, entries 9 & 10). Addition of TPP was needed for each cycle because, during regeneration of the catalyst with hydrochloric acid solution, the TPP formed phosphonium salts which were lost during the regeneration process. The loss of phosphonium salts into the aqueous wash phase was confirmed by proton nuclear magnetic resonance. ICP-AES results showed that <0.01% phosphorous content was present in the sbc-FA products.

We have described the skeletal isomerization of normal chain unsaturated fatty acids to sbc-FAs using Lewis base modified zeolite-catalysts. The process can be used effectively to isomerize readily available monounsaturated fatty acids. This is important as currently most lubricants are petroleum-based and their potential release into the environment can cause severe environmental burden owing to the poor biodegradability of petroleum-based lubricants and hydraulic fluids. This process could benefit those interested in substituting the sbc-FAs for the petroleum based materials.

Our results were superior to those previously reports because we obtained much higher molar conversions of oleic acid (>95%) and selectivities to sbc-FA products (about 70 to 80 wt %). The undesirable dimer coproduct was also obtained at much lower yield (about 5-10 wt %). The literature results typically only gave moderate conversions and selectivity. We have also shown that the catalysts were recyclable and reusable for at least ten times without significant loss of activity and selectivity.

All of the references cited herein, including U.S. Patents, are incorporated by reference in their entirety. Also incorporated by reference in their entirety are the following references: U.S. Pat. No. 5,677,473; U.S. Pat. No. 5,713,990; U.S. Pat. No. 6,946,567; U.S. Patent Application Publication 2003/0191330; EP 0774451A1 (1996); Bekkem, H. V., et al., Introduction to Zeolite Science and Practice, 2nd Edn., Elsevier, New York, N.Y., 2001, pp. 1033-1053; Carole, T. M., et al., Applied Biochemistry and Biotechnology. 113-116: 871-885 (2004); Erhan, S. Z., and M. O. Bagby, J. Am. Oil Chem. Soc., 68(9): 635-638 (1991); Erhan, S. Z., et al., J. Am. Oil Chem. Soc., 69(3): 251-256 (1992); Hill, K., Pure Appl. Chem., 79: 1999-2011 (2007); Ngo, H. L., et al., Eur. J. Lipid Sci. Technol., 108: 214-224 (2007); Swern, D., Baily's Industrial Oil and Fat Products, Third Edition, John Wiley & Sons, New York; Tolman, C. A., Chem. Rev., 77: 313-348 (1977); Zhang, Z., et al., J. Surf. Detergents, 7: 211-215 (2004).

Thus, in view of the above, the present invention concerns (in part) the following:

A process for preparing saturated branched chain fatty acids or alkyl esters thereof comprising (or consisting essentially of or consisting of) subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a stericly hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction; wherein the yield of said saturated branched chain fatty acids is ≥70 wt %; wherein said stericly hindered Lewis base is a tertiary amine or phosphine with linear or branched C1 to C6 alkyl or phenyl groups attached thereto.

The above process wherein said process produces ≤about 10 wt % dimers.

The above process wherein said Lewis base is selected from the group consisting of amine, phosphine, triarylphosphine, dialkylarylphosphine, trialkylphosphine, and mixtures thereof. The process wherein said phosphine is selected from the group consisting of methylphosphine, butylphosphine, dibutylphosphine, tributylphosphine, phenylphosphine, diphenylphosphine, and mixtures thereof. The process wherein said triarylphosphine is selected from the group consisting of triphenylphosphine, diphenylphosphine, tri-p-tolylphosphine, tri(o-tolyl)phosphine, tri-m-tolylphosphine, trixylyl-phosphine, tris(p-ethylphenyl)phosphine, tris(p-methoxyphenyl)phosphine, tris(4-fluorophenyl)phosphine, tris(4-methoxyphenyl)phosphine, tris(dimethylamino)phosphine, tris(trimethylsilyl)phosphine, triisopropylphosphine, and mixtures thereof. The process wherein said dialkylarylphosphine is selected from the group consisting of di-n-butylphenylphosphine, dicyclohexylphenylphosphine, and mixtures thereof. The process wherein said trialkylphosphine is selected from the group consisting of tri-n-butylphosphine, tricyclohexylphosphine, tri-n-octylphosphine, trimethyphosphine, triethylphosphine, triisopropylphosphine, tricyclopentylphosphine, and mixtures thereof. The process wherein said amine is selected from the group consisting of dimethylamine, trimethylamine, diethylamine, triethylamine, diisopropylamine, triisopropylamine, triphenylamine, diphenylamine, and mixtures thereof.

The above process further comprising (or consisting essentially of or consisting of) a step wherein branched unsaturated fatty acids or alkyl esters thereof obtained by the skeletal isomerization reaction are hydrogenated to yield branched saturated fatty acids or alkyl esters thereof.

The above process wherein said unsaturated fatty acids have 16 to 22 carbon atoms.

The above process, wherein said process further comprises (or consists essentially of or consists of) recycling said catalyst by washing said catalyst with a solvent and heating said catalyst in an acid solution, recovering said catalyst, washing said catalyst with deionized water, and drying said catalyst. The process, wherein said solvent is a polar solvent or nonpolar solvent. The process, wherein said catalyst is heated in an acid solution at about 55° C. (e.g., 55° C.) for about 24 hours (e.g., 24 hours). The process, wherein said catalyst is dried at about 115° C. (e.g., 115° C.) for about 20 hours (e.g., 20 hours). The process, wherein the recycled catalyst has about 2 to about 5% (e.g., 2 to 5%) loss of activity and selectivity.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Isomerization of oleic acid with 2.5 wt % H-Ferr and various amount of TPP.[1]

| Entry | TPP (wt % to zeolite) | Reaction Conditions Temp [° C.] Time [h] | Methyl Iso-stearate [2] | Methyl Stearate [3] | Methyl Hydroxy-stearate [4] | γ-Stearo-lactone [5] | $C_{36}$-Methyl Ester Dimer [6] | Conversion [%][2] |
|---|---|---|---|---|---|---|---|---|
| 1[3] | none | 250, 6.0 | 82 | 5.9 | 5.2 | 1.2 | 5.5 | >99 |
| 2[4] | none | 250, 6.0 | 71.5 | 5.93 | 7.29 | 1.68 | 13.6 | >99 |
| 3 | 2.5 | 250, 6.0 | 48.1 | 32 | 7.36 | 9.36 | 3.8 | 72 |
| 4 | 2.5 | 250, 22 | 77.2 | 6.58 | 7.73 | 2.16 | 6.33 | 99 |

TABLE 1-continued

Isomerization of oleic acid with 2.5 wt % H-Ferr and various amount of TPP.[1]

| Entry | TPP (wt % to zeolite) | Reaction Conditions Temp [° C.] Time [h] | Methyl Iso-stearate [2] | Methyl Stearate [3] | Methyl Hydroxy-stearate [4] | γ-Stearo-lactone [5] | $C_{36}$-Methyl Ester Dimer [6] | Conversion [%][2] |
|---|---|---|---|---|---|---|---|---|
| 5 | 5.0 | 250, 22 | 76.5 | 6.62 | 9.82 | 1.60 | 5.46 | 99 |
| 6 | 20 | 250, 22 | 70.1 | 10.6 | 10.1 | 4.78 | 4.44 | 95 |
| 7 | none | 280, 6.0 | 66.5 | 4.46 | 5.49 | 0.75 | 22.8 | >99 |
| 8 | 2.5 | 280, 6.0 | 76.9 | 5.98 | 7.87 | 2.01 | 7.24 | >99 |
| 9 | 5.0 | 280, 6.0 | 77.4 | 6.64 | 7.66 | 2.04 | 6.26 | 99 |
| 10 | 10 | 280, 6.0 | 79.2 | 7.17 | 6.73 | 1.60 | 5.30 | 98 |
| 11[5] | 10 | 280, 6.0 | 77.0 | 7.79 | 6.93 | 1.53 | 6.75 | 98 |
| 12 | 20 | 280, 6.0 | 73.8 | 8.97 | 8.35 | 2.67 | 6.21 | 97 |
| 13[6] | 20 | 280, 8.0 | 78 | 10.5 | 4.28 | 2.75 | 4.47 | 95 |

[1]GC data collected on the intact reaction product after isomerization, hydrogenation and methylation using methyl tridecanoate as internal standard. TPP = Triphenylphosphine. Isolated yields for all reactions were >98%.
[2]Conversion calculated as 94.3 − [(methyl stearate − 5.74)]/94.3 X 100[94.3 is the total unsaturated fatty acids in the starting fatty acids (oleic acid). 5.74 is the fatty acids in the oleic acid which do not contribute to the reaction].
[3]Results were previously reported in Ngo et al.
[4]Results obtained using modified GC method.
[5]Replicate of entry 10.
[6]Reaction was performed at 200g scale.

TABLE 2

Isomerization of oleic acid with 8 wt % H-Mordenite and various amount of TPP.[1]

| Entry | TPP [wt % to zeolite] | Reaction Conditions Temp [° C.] Time [h] | Methyl Iso-stearate [2] | Methyl Stearate [3] | Methyl Hydroxy-stearate [4] | γ-Stearo-lactone [5] | C36-Methyl Ester Dimer [6] | Conversion [%][2] |
|---|---|---|---|---|---|---|---|---|
| 1[3] | None | 280, 6.0 | 66.5 | 5.05 | 2.84 | 0.10 | 25.6 | >99 |
| 2 | 5.0 | 280, 6.0 | 74.1 | 6.71 | 3.83 | 1.26 | 14.1 | 99 |
| 3 | 10 | 280, 6.0 | 77.6 | 7.08 | 4.02 | 1.49 | 9.81 | 99 |
| 4 | 5.0 | 250, 6.0 | 68.3 | 14.5 | 3.60 | 5.82 | 7.78 | 91 |

[1]GC data collected on the intact reaction product after isomerization, hydrogenation and methylation using methyl tridecanoate as internal standard. TPP = Triphenylphosphine.
[2]Conversion calculated as 94.3− [(methyl stearate − 5.74)]/94.3 X 100 [94.3 is the total unsaturated fatty acids in the starting fatty acids (oleic acid). 5.74 is the fatty acids in the oleic acid which do not contribute to the reaction].
[3]Since the patent did not report the other components, we decided to repeat the experiment under the conditions as reported by Tomifuji et al.[9]

TABLE 3

Catalyst recycle experiments (isomerization of Priolene ).[1]

| Entry | run | TPP (wt % to zeolite) | Methyl Isostearate [2] | Methyl Stearate [3] | Methyl Hydroxystearate [4] | γ-Stearo-lactone [5] | $C_{36}$-Methyl Ester Dimer [6] | Conversion [%][2] |
|---|---|---|---|---|---|---|---|---|
| 1 | 1 | 7.5 | 79.7 | 6.0 | 6.57 | 2.14 | 5.59 | >99 |
| 2 | 2 | 5.0 | 80.0 | 5.75 | 6.48 | 2.12 | 5.65 | >99 |
| 3 | 3 | 5.0 | 79.4 | 5.21 | 7.51 | 1.79 | 6.09 | >99 |
| 4 | 4 | 5.0 | 81.1 | 5.98 | 6.62 | 1.91 | 4.39 | >99 |
| 5 | 5 | 5.0 | 80.8 | 5.76 | 6.70 | 1.60 | 5.06 | >99 |
| 6 | 6 | 5.0 | 81.5 | 7.65 | 4.83 | 2.06 | 3.96 | 98 |
| 7 | 7 | 5.0 | 79.3 | 7.11 | 5.07 | 2.32 | 6.20 | 99 |
| 8 | 8 | 5.0 | 81.8 | 7.24 | 4.25 | 1.91 | 4.80 | 98 |
| 9 | 9 | 5.0 | 78.3 | 9.96 | 4.0 | 3.36 | 4.38 | 96 |
| 10 | 10 | 5.0 | 75.0 | 12.0 | 3.69 | 4.42 | 4.89 | 93 |

[1]GC data collected on the intact reaction product after isomerization, hydrogenation and methylation using methyl tridecanoate as internal standard. TPP = Triphenylphosphine. Reactions were carried with 5 wt % H-Ferr, TPP, 1.8 mL deionized water at 260° C. for 4 h.
[2]Conversion calculated as 94.3 −[(methyl stearate − 5.74)]/94.3 X 100[94.3 is the total unsaturated fatty acids in the starting fatty acids (Priolene). 5.74 is the fatty acids in the Priolene which do not contribute to the reaction].

TABLE 4

Selected properties of sbc-FAs from ERRC and a commercial vender.

| | | Samples from ERRC | | | Samples from Private Sector | | |
|---|---|---|---|---|---|---|---|
| | | A | B | C | D | E | |
| | | sbc-FAs | sbc-FAs | Distilled sbc-FAs | Commercial | Commercial | Analytical Method |
| Entry | Analysis | (H-Mordenite)[1] | (H-Ferr)[2] | (H-Ferr)[3] | Product[4] | Product[4] | [ASTM D] |
| 1 | Acid value (mg KOH/gm) | 137 | 165 | 175 | 187 | 190 | 1980-87 |
| 2 | Saponification value (mg KOH/gm) | 169 | 186 | 190 | 194 | 195 | 1962-85 |
| 3 | Iodine value (IV) | 12 | 3.1 | 1.1 | 3.6 | 1.6 | 1959-85 |
| 4 | Water content (%) | 0.08 | 0.02 | 0.01 | 0.03 | 0.02 | 1744-92 |
| 5 | Cloud point (°C.) | 11 | 6.3 | 7.8 | 3.9 | 1.9 | 2500-81 5771-95 |

[1] % composition is 84 wt % methyl isostearate (2), 6.2 wt % methyl stearate (3), 3.3 wt % methyl hydroxystearate (4), 1.1 wt % γ-stearolactone (5), 5.4 wt % C36-methyl ester dimer (6).
[2] % composition is 86 wt % methyl isostearate (2), 2.1 wt % methyl stearate (3), 7.7 wt % methyl hydroxystearate (4), 1.9 wt % γ-stearolactone (5), 2.9 wt % C36-methyl ester dimer (6).
[3] Distilled sbc-FA materials from sample B with the following composition: 88.2 wt % methyl isostearate (2), 3.4 wt % methyl stearate (3), 6.2 wt % methyl hydroxystearate (4), 2.2 wt % γ-stearolactone (5).
[4] Sbc-FA products without dimer acid contaminants.

We claim:

1. A process for preparing saturated branched chain fatty acids or alkyl esters thereof comprising subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a sterically hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction; wherein the yield of said saturated branched chain fatty acids is ≥70 wt %; wherein said sterically hindered Lewis base is a tertiary amine or phosphine with linear or branched C1 to C8 alkyl or phenyl groups attached thereto.

2. The process according to claim 1, wherein said process produces ≤about 10 wt % dimers.

3. The process according to claim 1, wherein said Lewis base is selected from the group consisting of methylphosphine, butylphosphine, dibutylphosphine, tributylphosphine, phenylphosphine, diphenylphosphine, triphenylphosphine, tri(p-tolyl)phosphine, tri(o-tolyl)phosphine, tri(m-tolyl) phosphine, trixylyl-phosphine, tris(p-ethylphenyl)phosphine, tris(p-methoxyphenyl)phosphine, tris(4-fluorophenyl)phosphine, tris(4-methoxyphenyl)phosphine, tris (dimethylamino)phosphine, tris(trimethylsilyl)phosphine, triisopropylphosphine, di-n-butylphenylphosphine, dicyclohexylphenylphosphine, tri-n-butylphosphine, tricyclohexylphosphine, tri-n-octylphosphine, trimethyphosphine, triethylphosphine, triisopropylphosphine, tricyclopentylphosphine, dimethylamine, trimethylamine, diethylamine, triethylamine, diisopropylamine, triisopropylamine, diphenylamine, triphenylamine, and mixtures thereof.

4. The process according to claim 1, further comprising a step wherein branched unsaturated fatty acids or alkyl esters thereof obtained by the skeletal isomerization reaction are hydrogenated to yield branched saturated fatty acids or alkyl esters thereof.

5. The process according to claim 1, wherein said unsaturated fatty acids have 16 to 22 carbon atoms.

6. The process according to claim 1, wherein said process further comprises recycling said catalyst by washing said catalyst with a solvent and heating said catalyst in an acid solution, recovering said catalyst, washing said catalyst with deionized water, and drying said catalyst.

7. The process according to claim 6, wherein said solvent is a polar solvent or non-polar solvent.

8. The process according to claim 1, wherein said catalyst is heated in an acid solution at about 55° C. for about 24 hours.

9. The process according to claim 6, wherein said catalyst is dried at about 115° C. for about 20 hours.

10. The process according to claim 6, wherein the recycled catalyst has about 2 to about 5 wt % loss of activity and selectivity.

11. The process according to claim 1, wherein said process consists essentially of subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a sterically hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction; wherein the yield of said saturated branched chain fatty acids is ≥70 wt %; wherein said sterically hindered Lewis base is a tertiary amine or phosphine with linear or branched C1 to C8 alkyl or phenyl groups attached thereto.

12. The process according to claim 1, wherein said process consists of subjecting unsaturated fatty acids having 10 to 25 carbon atoms, alkyl esters thereof or mixtures thereof to a skeletal isomerization reaction in the presence of water or a lower alcohol at a temperature of about 240° C. to about 280° C. using a combination of a sterically hindered Lewis base and zeolite as a Brönsted or Lewis acid catalyst, and isolating saturated branched chain fatty acids or alkyl esters thereof or mixtures thereof from the reaction mixture obtained by the skeletal isomerization reaction; wherein the yield of said saturated branched chain fatty acids is ≥70 wt %; wherein said sterically hindered Lewis base is a tertiary amine or phosphine with linear or branched C1 to C8 alkyl or phenyl groups attached thereto.

* * * * *